United States Patent [19]

Szmuszkovicz

[11] 4,169,156
[45] Sep. 25, 1979

[54] N-(2-AMINOCYCLOHEPTYL)AL-KANOYLANILIDES

[75] Inventor: Jacob Szmuszkovicz, Kalamazoo, Mich.

[73] Assignee: The Upjohn Company, Kalamazoo, Mich.

[21] Appl. No.: 912,643

[22] Filed: Jun. 5, 1978

Related U.S. Application Data

[63] Continuation-in-part of Ser. No. 885,515, Mar. 13, 1978, which is a continuation-in-part of Ser. No. 779,593, Mar. 21, 1977, abandoned.

[51] Int. Cl.² .................. A61K 31/22; A61K 31/165; C07C 155/03; C07C 157/07
[52] U.S. Cl. .............................. 424/324; 260/455 A; 260/557 R; 260/562 A; 260/562 R; 424/311; 560/27
[58] Field of Search ................ 424/324, 311; 260/552, 260/455 A, 557 R, 562 A, 562 R; 560/27

[56] References Cited

U.S. PATENT DOCUMENTS 3,510,492  5/1970  Szmuszkovicz .................. 260/293.79

Primary Examiner—Stanley J. Friedman
Attorney, Agent, or Firm—John T. Reynolds

[57] ABSTRACT

N-(2-aminocycloheptyl)N-alkanoylanilides and their 2-N-oxides of the formula

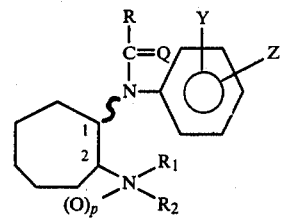

e.g., trans-3,4-dichloro-N-[2-(allylamino)cycloheptyl]-propionanilide, and their pharmacologically acceptable salts, have been found to possess potent Central Nervous System antidepressant properties. Many of them are new.

These compounds are promising antidepressant drugs which are characterized by lower toxicity than imipramine, and long acting activity which may allow longer durations between administrations, e.g., once a day. Pharmaceutical compositions containing these compounds and a process for treating conditions of depression with these compositions are disclosed.

24 Claims, No Drawings

N-(2-AMINOCYCLOHEPTYL)ALKANOYLANILIDES

CROSS REFERENCE TO RELATED APPLICATIONS

This is a continuation-in-part application of U.S. patent application Ser. No. 885,515, filed Mar. 13, 1978, which is a continuation-in-part of application Ser. No. 779,593, filed Mar. 21, 1977, now abandoned.

INTRODUCTION

This invention relates to amino-cycloaliphatic amides which have central nervous system pharmaceutical utility. More particularly this invention provides some new pharmaceutical preparations containing cis and/or trans N-(2-aminocycloheptyl)-N-alkanoylanilide compounds or their pharmacologically acceptable salts which have been found to have potent central nervous system (CNS) antidepressant properties which makes them useful as antidepressant drugs, when formulated into useful pharmaceutically usable composition forms, and administered in appropriate dosages.

BACKGROUND OF THE INVENTION

W. G. Stoll et al., in *Helvetica Chemica Acta*, Vol. 34, (1951), pp. 1937 to 1943 disclose N-[2-(dimethylamino)-cyclohexyl]aniline and procedures for making it from N-(2-hydroxycyclohexyl)aniline and suggest that the compounds therein have antihistamine pharmacological properties, but nothing is said about the compounds of this invention or their use as antidepressant drugs.

J. W. Lewis et al., in an article entitled "The Reactions of Aromatic Nitroso-compounds with Enamines. Part I. The Reaction of Nitrosobenzene with 1-Morpholin-1-cyclohexene" in *J. Chem. Soc.* (London) (1972), Perkins Transactions I, Part III, pp. 2521–2524 discloses inter alia N-(2-morpholin-1-ylcyclohexyl)-phenylhydroxylamine and its hydrochloride salt, but it does not disclose or suggest the alkanoylanilides of this invention or their antidepressant properties.

J. W. Lewis et al., in an article entitled "Chemistry and Biological Activity of N-Substituted Hydroxylamines" in *J. Pharmaceutical Sciences*, December, 1974, Vol. 63, No. 12, pp. 1951–1953 discloses some N-arylhydroxylamines such as N-[2-(N-pyrrolidinyl)cyclohexyl]-N-phenylhydroxylamine but these do not have useful CNS properties. Diuretic activity is alleged therein for the alcohols such as [2-(N-piperidinyl)cyclohexyl](4-methoxyphenyl)methanol and when the alcohol is acetylated, CNS depressant activity is said to appear. It also discloses the reaction of propionyl chloride with N-[2-(N-piperidinyl)-1,1-dimethylethyl]-N-phenylhydroxylamine to form the N-chloro compound which is then converted to a mixture of chlorinated aniline derivatives. That publication does not teach the compounds disclosed herein, how to make them, nor does it suggest the antidepressant properties which have been found for the compounds disclosed and claimed herein.

Szmuszkovicz U.S. Pat. No. 3,510,492 discloses and claims some 2-anilino- and 2-anilinomethylcycloalkylamines which are useful as antidiabetic drugs in that they can be administered in low dosages for reducing blood sugar. However, that patent in column 2, structure IV generically suggests some of the formula I compounds of the pharmaceutical preparations and use process of this invention as chemical intermediates enroute to the 2-anilinocycloalkyl amines thereof, but it does not suggest any end product practical utility for those structures IV compounds and it does not disclose the compounds claimed herein.

OBJECTS OF THE INVENTION

It is an object of this invention to provide some new N-(2-aminocycloheptyl)alkanoylanilides which have been found to have promising antidepressant drug properties.

It is a more specific object of this invention to provide new N-(2-aminocycloheptyl)alkanoylanilides which are useful as antidepressant drugs, the preferred compounds having lower toxicity than imipramine and longer lasting activity which allows longer durations between administrations.

It is another object of this invention to provide compositions, useful in pharmaceutical dosage unit form, for treating conditions of depression in mammals including humans comprising an N-(2-aminocycloheptyl)alkanoylanilide as described herein, or a pharmacologically acceptable salt thereof in a pharmaceutical carrier.

It is another object of this invention to provide a process for treating conditions of depression in mammals including humans with these compositions containing an N-(2-aminocycloheptyl)alkanoylanilide, or a pharmacologically acceptable salt thereof.

Other objects, aspects and advantages of this invention will be apparent from reading the specification and claims which follow.

SUMMARY OF THE INVENTION

Briefly, this invention provides pharmaceutical preparations of some cis and trans N-(2-aminocycloheptyl)-N-alkanoylanilides of the formula

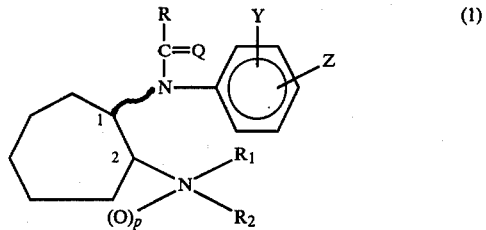

and their pharmacologically acceptable salts, wherein p, Q, R, $R_1$, $R_2$, Y and Z are as defined hereinbelow, which have been found to possess potent central nervous system (CNS) antidepressant properties. A preferred example for this use is trans-3,4-dichloro-N-[2-(allylamino)cycloheptyl]propionanilide. This invention also includes these compounds (I) which are new, per se, and their acid addition salts, especially their pharmacologically acceptable salts. These compounds are useful, in appropriate pharmaceutical dosage unit form, for administration to humans in dosages of from 4–400 mg. per day as part of the therapy in treating conditions of depression. In standard laboratory animals used to determine these properties, these compounds suggest fast onset of the antidepressant characteristics of the drug, the preferred compounds having, in addition, lower toxicity than a standard antidepressant drug, imipramine, in standard laboratory tests, and longer duration of activity of the test compound in the test animal. These characteristics of these compounds will make them useful for the administration of these compounds as antidepressant drugs in smaller amount and/or for longer durations between administration, e.g., once a day, for a given desired antidepressant response.

This invention also includes a process for treating depression with these compositions containing these above formula I compounds, or pharmaceutically acceptable salts thereof, and a pharmaceutical carrier, which compositions are useful in dosage unit form for treating conditions of depression in mammals including humans.

DETAILED DESCRIPTION OF THE INVENTION

More specifically, one aspect of this invention provides new pharmaceutical preparations containing compounds of the formula

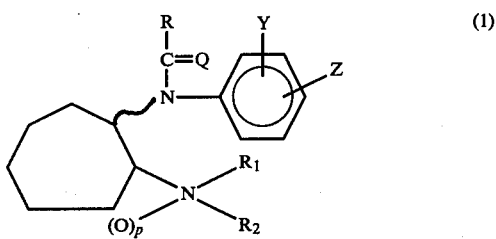

wherein the wavy line ($\sim$) on the 1-position of the cycloheptyl ring denotes cis- or trans-configuration relative to the amino group in the 2-position of the cycloheptyl ring;

p is zero or 1;

Q is oxygen or sulfur;

R is $C_1$ to $C_3$-alkyl, $C_3$ to $C_6$-cycloalkyl, vinyl (—CH—$CH_2$), ethoxy or methoxymethyl;

$R_1$ is hydrogen or $C_1$ to $C_3$-alkyl;

and when $R_1$ is hydrogen or $C_1$ to $C_3$-alkyl;

$R_2$ can be

—$CH_2C_6H_5$(benzyl),
—$CH_2CH_2$-$C_6$-$H_5$ (2-phenylethyl), or
—$C_3$-$C_6$-(allylic)alkenyl and when $R_1$ and $R_2$ are taken together with the nitrogen to which they are bonded, they complete an N-pyrrolidinyl or an N-piperidinyl ring;

each of Y and Z is selected from the group consisting of hydrogen, a halogen having an atomic number of from 9 to 35, trifluoromethyl, $C_1$ to $C_2$-alkyl, and $C_1$ to $C_2$-alkyloxy, and when Y is trifluoromethyl Z is hydrogen; when Y is $C_1$ to $C_2$-alkyloxy and Z is hydrogen, the $C_1$ to $C_2$-alkyloxy is in the 3-position; when Y and Z are both halogens or $C_1$ to $C_2$-alkyloxy, they are present in 3- and 4- or 3- and 5-positions, and the acid addition salts thereof, preferably the pharmacologically acceptable acid addition salts thereof. On occasion, the compounds or their acid addition salts in their crystalline state are isolated as solvates, i.e., with a discrete quantity of solvent, e.g., water, ethanol, and the like, associated physically, and thus the solvent is removable without effective alteration of the chemical entity per se and are included with the compounds per se herein.

In the above formula I compounds, the term "$C_1$ to $C_3$-alkyl" means methyl, ethyl, n-propyl and isopropyl; the term "$C_3$ to $C_6$-cycloalkyl" means cyclopropyl, cyclobutyl, cyclopentyl and cyclohexyl groups; the term "$C_3$ to $C_6$-(allylic)alkenyl" includes the non-adjacent double bond groups, e.g., allyl, 2-butenyl and 2-methyl-2-butenyl, 2-pentenyl and 3-methyl-2-pentenyl, and the various 2-hexenyl groups; and the halogens having atomic numbers of from 9 to 35 are fluorine, chlorine and bromine.

The preferred compounds of this invention are those of the trans configuration.

A preferred subgroup of the above compounds and the pharmaceutical preparation forms thereof are those wherein R is $C_1$ to $C_3$-alkyl, preferably ethyl; $R_1$ and $R_2$ are each $C_1$ to $C_3$ alkyl; and at least one of Y and Z are halogen having an atomic number of from 9 to 35, preferably in the 3- and 4- positions, $C_1$ to $C_2$-alkyloxy or trifluoromethyl in the 3-position, or methyl in the 3- or 4-position in combination with one of the above halogens at the adjacent 3- or 4-position, and the pharmacologically acceptable salts thereof. Examples of such compounds include the following:

3,4-dichloro-N-[2-(dimethylamino)cycloheptyl]propionanilide;

3-trifluoromethyl-N-[2-(dimethylamino)cycloheptyl]propionanilide, 3,4-dichloro-N-[2-(diethylamino)cycloheptyl]propionanilide, 3-chloro-4-methyl-N-[2-(dimethylamino)cycloheptyl]propionanilide, 4-chloro-3-methyl-N-[2-(diethylamino)cycloheptyl]propionanilide, 3-chloro-N-[2-(dimethylamino)cycloheptyl]propionanilide, 4-chloro-N-[2-(dimethylamino)cycloheptyl]propionanilide, 3-methoxy-4-chloro-N-[2-(dimethylamino)cycloheptyl]propionanilide, 3-methoxy-N-[2-(dimethylamino)cycloheptyl]propionanilide, 3-bromo-N-[2-(dimethylamino)cycloheptyl]propionanilide, and 3-fluoro-N-[2-(dimethylamino)cycloheptyl]propionanilide, especially these compounds in the trans configurations, and the pharmacologically acceptable salts thereof.

Another preferred sub-group of the above compounds are those wherein R is $C_1$ to $C_3$-alkyl, preferably ethyl, $R_1$ and $R_2$ are taken together with the nitrogen to which they are bonded to complete an N-pyrrolidinyl or N-piperidinyl ring, and at least one of Y and Z is a halogen having an atomic number of from 9 to 35 in the 3- and/or 4-positions. Examples of such compounds include:

3-fluoro-N-[2-(N-pyrrolidinyl)cycloheptyl]propionanilide, 3,4-dichloro-N-[2-(N-piperidinyl)cycloheptyl]propionanilide;

3-bromo-N-[2-(N-pyrrolidinyl)cycloheptyl]propionanilide, 4-chloro-N-[2-(N-pyrrolidinyl)cycloheptyl]propionanilide, 3,4-dichloro-N-[2-(N-pyrrolidinyl)cycloheptyl]propionanilide, 3,4-difluoro-N-[2-(N-pyrrolidinyl)cycloheptyl]propionanilide, and 3,4-dibromo-N-[2-(N-pyrrolidinyl)cycloheptyl]propionanilide, especially these compounds in their trans configuration and the pharmacologically acceptable salts thereof.

Another preferred sub-group of the above compounds are those wherein R is $C_3$ to $C_6$-cycloalkyl, $R_1$ and $R_2$ are $C_1$ to $C_3$-alkyl, and at least one of Y and Z are halogen having an atomic number of from 9 to 35 in the 3- or 4-position, trifluoromethyl in the 3-position, or methyl in the 3- or 4- position in combination with one of the above halogens in the adjacent 3- or 4-positions, and the pharmacologically acceptable salts thereof. Examples of such compounds include:

3,4-dichloro-N-[2-dimethylaminocycloheptyl]cyclobutanecarboxanilide, 3,4-dichloro-N-[2-dimethylaminocycloheptyl]cyclohexanecarboxanilide, 3-bromo-4-methyl-N-[2-dimethylaminocycloheptyl]-cyclobutanecarboxanilide, 3,4-dichloro-N-[2-dimethylaminocycloheptyl]cyclopropanecarboxanilide, 3-trifluoromethyl-N-[2-diethylaminocycloheptyl]cyclopropanecarboxanilide, 3,4-dibromo-N-[2-diethylaminocycloheptyl]cyclopropanecarboxanilide, 3-chloro-4-methyl-N-[2-dimethylaminocycloheptyl]-clopropanecarboxanilide, 3-bromo-4-methyl-N-[2-dimethylaminocycloheptyl]-cyclohexanecarboxanilide, 3-trifluoromethyl-N-[2-dimethylaminocycloheptyl]-cyclohexanecarboxanilide, and the pharmacologically acceptable salts thereof.

Examples of acid addition salts, including pharmacologically acceptable salts of the above formula I compounds include those of hydrochloric, methanesulfonic, pamoic, hydrobromic, sulfuric, acetic, cyclohexanesulfamic, p-toluenesulfonic, succinic, β-naphthalenesulfonic, maleic, fumaric, citric, lactic and oxalic acids.

To use these new compounds in pharmaceutical antidepressant drug product form they are compounded or formulated into usual pharmaceutical compositions, e.g., oral dosage forms such as tablets, powders, capsules and solutions or suspensions in a suitable solvent or suspending vehicle, and parenteral dosage forms such as dry powder in a sterile sealed container to be mixed with a sterile solvent just prior to administration, sterile solutions or suspensions in water or other suitable solvents or suspending agents, to provide a convenient means for administering to the patient in an amount effective to alleviate the conditions of depression, in association with a pharmaceutical carrier. Generally, daily doses ranging from about 4 mg. to about 400 mg., preferably 50 to 200 mg., of the formula I compound or its pharmacologically acceptable salt, depending upon the potency of the formula I compound, the condition being treated, the weight of the patient and other factors of concern to the patient's physician would be given to such patients.

The formula I compounds where Q is oxygen (=O) and p is zero can be prepared by (a) heating a mixture of a compound of the formula

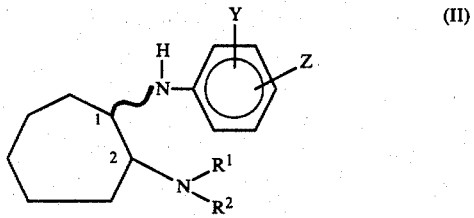

(II)

wherein $R_1$, $R_2$, Y and Z are as defined above, and an anhydride of the appropriate organic carboxylic acid of the formula R—COOH on a steam bath, or at an equivalent temperature, for a time sufficient to form the N-acylated product of formula I where R is as defined above, Q is oxygen and p is zero, (b) adding an aqueous medium to the step (a) reaction mixture in an amount sufficient to decompose excess anhydride therein, (c) adding an alkali metal hydroxide or its equivalent to the step (b) reaction mixture in an amount sufficient to neutralize excess acid present therein and to make the mixture pH basic, (d) extracting the N-acylated product (I) into a water immiscible organic liquid solvent, e.g., ether solvents such as diethyl ether, terahydrofuran (THF) or dioxane, or chloroform, carbon tetrachloride, methylene chloride, ethylene dichloride, or the like (e) separating the organic liquid phase containing the N-acylated product (I) from the aqueous phase, and (f) recovering the corresponding N-acylated compound (I) from the organic liquid phase, usually after washing the organic liquid phase one or more times with aqueous media such as sodium chloride solution, sodium bicarbonate solution or water to extract components soluble in those aqueous media, separating the aqueous phases, drying the washed organic phase with drying agents such as magnesium sulfate or sodium or calcium sulfate, and then evaporating off the organic solvent. Further purification can be done by forming an acid salt of the N-acylated amide product (I) and then recrystallizing the amide salt from an appropriate solvent or mixture of solvents.

These formula I compounds, immediately above, can also be prepared by (a) adding a solution of the appropriate carboxylic acid halide R—C(O)—X where R is as defined above and X is chloride or bromide to a cooled (−5° to +10° C.) mixture of the diamine (II), and a tertiary amine which will form a tertiary amine chloride or bromide salt in the mixture, e.g., a $C_1$ to $C_4$-trialkylamine, e.g., trimethylamine, triethylamine, tributylamine, or pyridine, lutidine, N,N-dimethylaniline or the like, in an organic liquid solvent for the mixture such as an ether solvent such as diethyl ether, THF, dioxane or the like, while agitating the mixture until the corresponding N-acylated compound (I) is formed, (b) adding an aqueous alkali metal bicarbonate solution to the reaction mixture of step (a), (c) separating the aqueous from the organic liquid phases, (d) washing the organic liquid phases with aqueous wash liquids as described above, (e) drying the organic phase, and (f) recovering the N-acylated compound (I) from the resulting organic liquid mixture. The N-acylated amide compound (I) can be further purified by formation of an acid addition salt thereof, e.g., the hydrochloric acid, or maleic acid addition salt thereof, and recrystallization of the amide salt from an appropriate solvent or solvent mixture.

The formula I compounds which do not contain a reactive aliphatic carbon-to-carbon double bond in the molecule, and wherein Q is oxygen (=O) and p is zero, can be converted to their N-oxides by reaction or such formula I aminoamide or its salt with a percarboxylic acid by known procedures to obtain the corresponding formula I compound where p is 1.

The corresponding N-thioacyl amino anilide compounds can be prepared by heating to reflux the corresponding N-acyl(C=O) amino anilide (formula I compound) with a thiolating agent such as phosphorus pentasulfide or diethyldithiophosphate [P(S)SH(OC$_2$H$_5$)$_2$] in an appropriate solvent such as pyridine for a time sufficient to effect replacement of the acyl oxygen atom with sulfur, and then recovering and purifying the N-thioacyl aminoanilide compound by known procedures. If the N-oxides of the Q is S compounds are to be made, the N-oxide is prepared first and the resulting N-oxide is thiolated as described above to form the formula I compound where Q is=S and p is 1.

Further exemplification of these process procedures appear in the detailed examples.

The trans-diamine starting materials (II) of the formula:

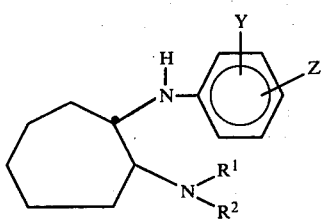

wherein $R_1$, $R_2$, Y and Z are as defined above can be prepared by reacting 1,2-cycloheptene oxide (IIIa)

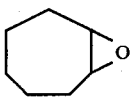

with the selected $HNR_1R_2$ amine in water to form the trans-2-aminocyclopentanol of the formula IIIb

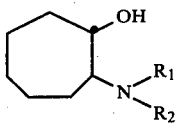

which amino-alcohol (IIIb) is treated with sodium hydride and then with methanesulfonyl chloride to form unrecovered mesylate of the formula IV

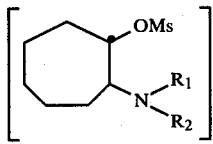

wherein Ms denotes $CH_3SO_2$-group and that reaction mixture is treated with the selected substituted aniline of formula V

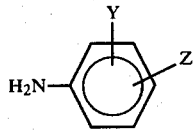

to form the diamine (II). Examples of this procedure are given hereinbelow in the detailed descriptions.

Examples of the carboxylic acid anhydrides which can be used to prepare the compounds of this invention include acetic anhydride, propionic anhydride, isobutanoic acid anhydride, n-butanoic acid anhydride, cyclopropanecarboxylic acid anhydride, acrylic acid anhydride, and the like. The preferred anhydride is propionic acid anhydride. The carboxylic acid halides are exemplified by acetyl chloride or bromide, propionyl chloride or bromide, acryloyl chloride or bromide, cyclohexanecarbonyl chloride or bromide, n- and isobutanoylchloride or bromide, cyclopropanecarbonyl chloride or bromide, ethyl formate, methoxyacetyl chloride or bromide, and the like. We have found that, in general, the most potent antidepressant compounds are made from those compounds having an N-propionyl moiety, so that in the formula I compound R is preferably ethyl.

When it is desired that the formula II have an allyl group in the $R_2$ position, an alternate method can also be used: the amino-amide is prepared as described above using an alkyl benzylamine to form the amino-alcohol (IIIb), and that amino-alcohol is carried through the intermediate (IV), and (V) reactions to form the diamine. The resulting diamine is then hydrogenated catalytically, preferably in the presence of palladium on carbon catalyst, to remove the benzyl group in the $R_2$ position and form the trans diamine of the formula VI.

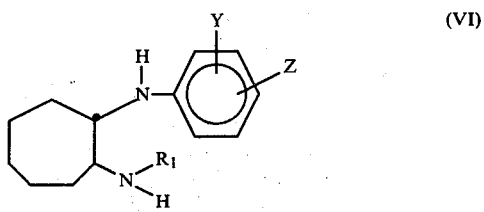

The trans-diamine (VI) is then reacted with a $C_3$-$C_6$(allylic)alkenyl chloride or bromide to form the compound of formula VII

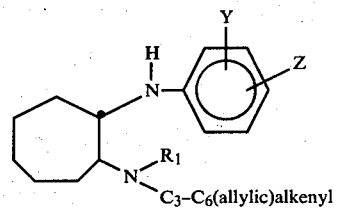

which diamine (VII) is used as an intermediate in a reaction with the selected carboxylic acid anhydride or acid chloride or bromide, to form the N-acylated product of the formula

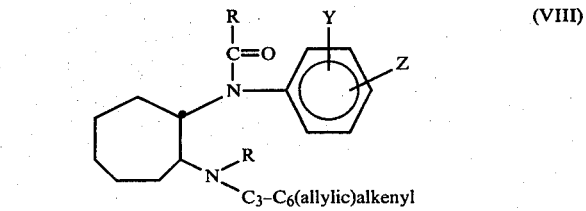

in which formulae Ia, IIIb, IV, V, VI, VII and VIII, R, $R_1$, Y and Z are as defined above.

Preparation of cis amino amide compound of invention:

The method of J. W. Lewis et al., J. Pharm. Sci., 63, 1951 (1974) using 1-dialkylaminocyclopentene (enamine) and nitrosoaryl as starting materials can be applied to the corresponding cycloheptene enamines to obtain cis-1,2-diaminocycloheptane which is subsequently reacted with carboxylic acid anhydride or carboxylic acid halide as described above to give the product amino-amide.

A preferred method, which is that used for this invention, involves reaction of cycloheptene oxide with an aniline in the presence of strong acid to give the compound of formula

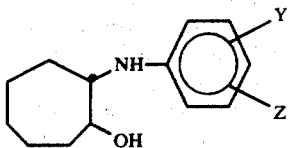

which is subsequently reacted with carboxylic acid anhydride followed by reaction with base to isolate the compound of formula

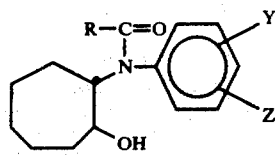

Oxidation of the alcohol leads to the compound of formula XI

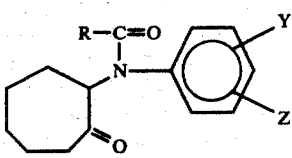

which when reacted with primary or secondary amine and a reducing agent such as sodium cyanoborohydride, and the like, gives a compound of the formula

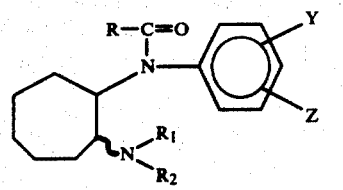

wherein $R_2$ is not $C_3$-$C_6$(allylic)alkenyl. The cis-/trans mixture of compounds which results can be separated physically by column chromatography on silica gel to isolate the cis-isomer of the formula

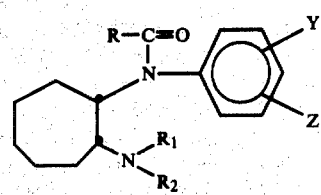

wherein R, $R_1$, $R_2$, Y and Z are as defined above. For the preparation of cis amino-amides wherein $R_2$ is $C_3$-$C_6$(allylic)alkenyl, the above sequence of steps is followed using a primary amine together with the reducing agent referred to above. After isolation of the cis amino amide, its reaction with a $C_3$-$C_6$(allylic)alkenyl halide yields the cis amino-amide wherein $R_2$ is $C_3$-$C_6$-(allylic)alkenyl.

The thio analogs of such cis amino-amides can be prepared as described earlier in this specification.

Examples of additional useful compounds of formula I of this invention include the following compounds, preferably in their trans-configuration N-[2-(dimethylamino)cycloheptyl]propionanilide, 3-methyl-N-[2-(dimethylamino)cycloheptyl]propionanilide, 3-methoxy-N-[2-(dimethylamino)cycloheptyl]propionanilide, 3,4-dichloro-N-{2-[N-methyl-N-(2-dimethylaminoethyl)amino]cycloheptyl}propionanilide, 3,4-dichloro-N-{2-[N-methyl-N-(3-dimethylaminopropyl)amino]cycloheptyl}propionanilide, N-[2-(dimethylamino)cycloheptyl]acetanilide, N-[2-(dimethylamino)cycloheptyl]butyranilide, 3-trifluoromethyl-N-[2-(N-methyl-N-benzylamino)cycloheptyl]propionanilide, 3,4-dibromo-N-{2-[N-ethyl-N-(2-phenylethyl)amino]cycloheptyl}propionanilide, 3-chloro-4-methyl-N-[2-(N-methyl-N-allylamino)cycloheptyl]propionanilide, 4-bromo-3-methyl-N-[2-(N-pyrrolidinyl)cycloheptyl]propionanilide, 3,4-difluoro-N-{2-[N-methyl-N-(2-dimethylaminoethyl)amino]cycloheptyl}propionanilide, 3-chloro-4-fluoro-N-[2-(dimethylamino)cycloheptyl]propionanilide, 3,4-dibromo-N-[2-(dimethylamino)cycloheptyl]propionanilide, 3,4-dimethyl-N-[2-(dimethylamino)cycloheptyl]propionanilide, 3,4-dichloro-N-[2-(dimethylamino)cycloheptyl]butyranilide, 3,4-dichloro-N-[2-(dimethylamino)cycloheptyl]-N-cyclopropanecarboxanilide, 3,4-dichloro-N-[2-(dimethylamino)cycloheptyl]thiopropionanilide, 3,4-dichloro-N-[2-(dimethylamino)cycloheptyl]-N-acrylanilide, 3,4-dichloro-N-[2-(dimethylamino)cycloheptyl]isobutyranilide, 3-bromo-N-[2-(N-methyl-N-benzylamino)cycloheptyl]butyranilide, 3-chloro-4-fluoro-N-[2-(N-pyrrolidinyl)cycloheptyl]cyclopropanecarboxanilide, 3,5-dibromo-N-[2-(N-methyl-N-2-phenylethylamino)cycloheptyl]propionanilide, 3,4-dichloro-N-[2-dimethylaminocycloheptyl]methoxyacetanilide, 3,4-dichloro-N-[2-dimethylaminocycloheptyl]carbethoxyanilide, 3-methyl-4-chloro-N-[2-diethylaminocycloheptyl]propionanilide, 3-trifluoromethyl-N-{2-[N-methyl-N-2-butenyl]aminocycloheptyl}cyclohexanecarboxanilide, 3-ethoxy-4-bromo-N-[2-dimethylaminocycloheptyl]propionanilide, 4-azido-N-[2-(dimethylamino)cycloheptyl]propionanilide.

and the like, the 2-N-oxides of the above compounds which do not contain aliphatic unsaturation, and their acid addition salts.

If desired, the formula I compounds of this invention can be resolved into their respective d- and l-optical isomers by methods known in the art. In this case the optical resolution can be done by at least two different routes. The resolving agents by either route are any of the known resolving agents such as optically active camphorsulfonic acid, bis-p-toluoyltartaric acid, tartaric acid, and diacetyl tartaric acid which are commercially available and which are commonly used for resolution of amines (bases) as for example in *Organic Syntheses,* Coll. Vol. V., p. 932 (1973), resolution of R-(+) and S-(−)-α-phenylethyl amine with (+)-tartaric acid.

By the first method for resolving the compounds of this invention, for example, one of the amino amide compounds can be converted into its optically active diastereomeric salts by reaction with an optically active acid, examples of which are mentioned above, in a manner standard in the isomer resolution art. These diastereomeric salts can then be separated by conventional means such as differential crystallization. Diastereomeric salts have different crystallization properties, which are taken advantage of in this separation. On neutralization of each diastereomeric salt with aqueous base, the corresponding optically active form of the free amino-amide can be obtained, each of which can subsequently and separately be converted as previously described in the examples to the desired acid addition salt.

By the second method, which in the case of some of these compounds is preferred, the formula I compounds can be made into their respective d- and l-isomers, by first resolving cis- or trans-1,2-cycloaliphatic unsymmetrically substituted diamine into its respective d- and l-isomers by treatment with the resolving agent, crystallization, separation, and regeneration of the respective trans-d-diamine, trans-l-diamine, or the cis-d-diamine and cis-l-diamine, and then reacting the respective resolved diamine starting material with the desired carboxylic acid anhydride or halide to form the respective cis- or trans-d- or l-compound of formula I, which can then be converted to any desired pharmaceutically acceptable acid addition salt by procedures exemplified above.

If the acid addition salt used to extract the formula I compound from its reaction mixture is not itself pharmacologically acceptable, the free amino-amide base (I) can be prepared from the acid salt, and thereafter converted to a pharmacologically acceptable salt, by known procedures.

In the use of these compounds of formula I as antidepressant drugs the selected compound of formula I is to be the antidepressant active ingredient is mixed with suitable pharmaceutical diluents to obtain pharmaceutical compositions suited for oral, parenteral and rectal use in dosage unit form, e.g., tablets, powder packets, cachets, dragees, capsules, solutions, suspensions, sterile injectable forms, suppositories, bougies, and the like. Suitable diluents or carriers such as carbohydrates (lactose), proteins, lipids, calcium phosphate, corn starch, stearic acid, methylcellulose and the like may be used as carriers or for coating purposes. Water and oils, e.g., coconut oil, sesame oil, safflower oil, cottonseed oil, peanut oil may be used for preparing solutions or suspensions of the active drug. Sweetening, coloring and flavoring agents may be added. The specifications for the dosage unit forms of these formula I compounds will vary somewhat from compound to compound and dependent upon the physical characteristics of the formula I compound or its pharmaceutically acceptable salt, the particular patient's weight and age, and the particular effect sought to be achieved. The pharmaceutical dosage unit forms of these compounds are prepared in accordance with the preceding general description to provide from about 4 to about 400 mg. of the formula I compound or its pharmacologically acceptable salt per dosage unit form. The amount of the formula I compound prescribed in pharmaceutical dosage unit form is that amount sufficient to obtain in the patient a relief from the condition of depression effect at a non-toxic dosage level.

The following detailed procedures and examples further describe and illustrate how to make and use the starting amines and the compounds of this invention. All temperatures are in degrees Centigrade unless otherwise indicated. For brevity, the term THF means tetrahydrofuran, NMR means nuclear magnetic resonance spectrum, IR means infrared spectrum, UV means ultraviolet spectrum, ether means diethyl ether, NaOH means sodium hydroxide, $MgSO_4$ means anhydrous magnesium sulfate, and MeOH means methanol.

EXAMPLE 1

Preparation of trans-3,4-dichloro-N-[2-(dimethylamino)cycloheptyl]-propionanilide and its maleate salt

A. Preparation of trans-2-dimethylaminocycloheptanol, and its fumarate salt

A mixture of 89.0 g. (0.80 mole) of cycloheptene oxide and 40% aqueous dimethylamine (275 ml., 2.4 mole) is shaken in a rocking pressure bomb at about 125° for 24 hours. A brown solution is obtained. The reaction mixture solution is then saturated with about 50 g. of potassium carbonate, and two layers are formed. One milliliter of 40% aqueous potassium hydroxide is added, the resulting mixture is extracted three times with ether, the ether layers are combined and dried with anhydrous magnesium sulfate and then concentrated by evaporation of ether. Distillation of the residue gives 114.6 g. (91% yield) of the titled amino alcohol, b.p. 98°–100°/10 mm. NMR, IR and mass spectrum analyses are in accord with the assigned structure.

The crystalline fumarate salt of the titled amino alcohol is prepared and recrystallized from methanol/ether, m.p. 136°–137° C.

Anal. Calcd. for $C_9H_{19}NO$ (Amino Alcohol): Calcd.: C, 68.74; H, 12.18; N, 8.91. Found: C, 68.48; H, 12.39; N, 8.53.

B. Preparation of trans-N-[2-(dimethylamino)cycloheptyl]-3,4-dichloroaniline, and its oxalic acid salt A mixture of 2-dimethylaminocycloheptan-1-ol (15.7 g., 0.10 mole) and 4.8 g. (0.10 mole) of sodium hydride (50% dispersion) in 50 ml. of THF is heated on a steam bath for one hour and then cooled in ice. Methanesulfonyl chloride (11.5 g., 0.10 mole) in 25 ml. of THF is added over 30 minutes. Subsequently, 3,4-dichloroaniline (32.4 g., 0.20 mole) is added in one portion. The THF solvent is removed by distillation and heating of the mixture on a steam bath is continued overnight. Addition of 200 ml. of 20% aqueous sodium hydroxide is followed by heating for one hour. The reaction mixture is extracted with 10% aqueous hydrochloric acid. The aqueous acid layer is washed with ether, basified with 40% aqueous sodium hydroxide and extracted with 250 ml. of ether. The ether layer is washed with saturated aqueous sodium chloride solution, dried with magnesium sulfate and the ether is removed by evaporation. The residual oil is distilled to give 17.3 g. (57% yield) of the titled amine (b.p. 170°–180°/0.3 mm).

The oxalic acid salt of the titled amine is prepared from 5.2 g. (0.057 mole) of oxalic acid and the diamine prepared above in a solvent mixture which consists of 25 ml. of methanol and 200 ml. of ether. Recrystallization from the same solvent mixture gives 15.5 g. (69% yield) of the oxalic acid salt of the titled diamine, m.p. 153°–154° C. The NMR, IR, UV and mass spectra are in accord with the assigned structure.

Anal. Calcd. for $C_{15}H_{22}N_2Cl_2 \cdot C_2H_2O_4$: Calcd.: C, 52.15; H, 6.18; N, 7.16; Cl, 18.12. Found: C, 52.25; H, 6.34; N, 6.98; Cl, 18.23.

C. Preparation of trans-3,4-dichloro-N-[2-(dimethylamino)cycloheptyl]-propionanilide and maleate salt To an ice-cooled solution of trans-N-[2-(dimethylamino)cycloheptyl]-3,4-dichloroaniline (3.01 g., 0.01 mole) and 2.02 g. (0.02 mole) of triethylamine in 100 ml. of ether there is added 1.85 g. (0.02 mole) of propionyl chloride over 30 minutes. The reaction mixture is stirred at room temperature overnight. Then 100 ml. of saturated sodium bicarbonate aqueous solution is added. The organic layer is washed with water followed by saturation sodium chloride solution and then dried over anhydrous magnesium sulfate and concentrated to a yellow oil residue of the titled propionanilide. This oil is dissolved in a mixture of methanol (10 ml.) and ether (75 ml.) and maleic acid (1.16 g., 0.01 mole) is added. A crystalline precipitate results which is recrystallized from the same solvent mixture to give 3.90 g. of the titled amino-anilide maleate salt (82% yield, m.p. 165°–166° C.). NMR, IR, UV and mass spectra are in accord with the structure.

Anal. Calcd. for $C_{18}H_{26}N_2Cl_2O \cdot C_4H_4O_4$: Calcd.: C, 55.81; H, 6.39; N, 5.92; Cl, 14.98. Found: C, 56.05; H, 6.46; N, 6.07; Cl, 15.16.

EXAMPLE 2

Preparation of trans 3-trifluoromethyl-N-[2-(1-pyrrolidinyl)cycloheptyl]-propionanilide Following the procedure of Example 1 but initially substituting in Part A a stoichiometric equivalent amount of pyrrolidine for the dimethylamine to obtain trans-2-(N-pyrrolidinyl)cycloheptanol and subsequently substituting in Part B a stoichiometric equivalent amount of 3-trifluoromethylaniline for the 3,4-dichloroaniline, there is obtained trans-N-[2-(N-pyrrolidinyl)cycloheptyl]-3-trifluoromethylaniline, which can be converted to its propionanilide and, if desired, to its acid addition salt such as the hydrochloride or maleate by the procedure of Example 1, Part C.

EXAMPLE 3

Preparation of trans-3,4-dichloro-N-[2-(dimethylamino)cycloheptyl]-propionanilide-2-N-oxide A stoichiometrically equivalent quantity of 85% m-chloroperbenzoic acid in chloroform is added dropwise to an equimolar amount of trans-3,4-dichloro-N-[2-(dimethylamino)cycloheptyl]propionanilide, prepared as described in Example 1, with ice cooling; the mixture is stirred overnight at room temperature and is then evaporated to dryness. After several washings and concentrations, the titled 2-N-oxide compound is obtained.

EXAMPLE 4

Preparation of trans-4-bromo-N-[2-(dimethylamino)cycloheptyl]thiopropionanilide Molar equivalent quantities of trans-4-bromo-N-[2-(dimethylamino)cycloheptyl]propionanilide, prepared analogously to the procedure described in Example 1, and phosphorous pentasulfide are dissolved in pyridine and the mixture is heated at the reflux temperature; the pyridine is removed by distillation and the title compound is isolated after weak basic and neutral work-up procedures. A maleic acid addition salt of such titled thio propionanilide is prepared according to the procedure of Example 1, Part C. Other acid addition salts can be similarly prepared.

EXAMPLE 5

Preparation of 3,4-dichloro-N-[2-(dimethylamino)cycloheptyl]thiopropionanilide The titled compound is prepared according to the procedure of Example 4 but substituting a stoichiometrically equivalent quantity of 3,4-dichloro-N-[2-(dimethylamino)cycloheptyl]propionanilide for 4-bromo-N-[2-(dimethylamino)cycloheptyl]propionanilide.

EXAMPLE 6

Preparation of cis-3,4-dichloro-N-[2-(dimethylamino)cycloheptyl]propionanilide

A. Preparation of trans-3,4-dichloro-N-[2-hydroxycycloheptyl]aniline

Following the procedure of Example 1, Part A, but substituting the appropriate quantity of 3,4-dichloroaniline for dimethylamine, the product trans-3,4-dichloro-N-[2-hydroxycycloheptyl]aniline is obtained.

B. Preparation of trans-3,4-dichloro-N-(2-hydroxycycloheptyl)propionanilide Following the procedure of Example 1, Parts B and C, but substituting the stoichiometrically equivalent quantities of trans-3,4-dichloro-N-[2-(hydroxy)cycloheptyl]aniline for trans-N-[2-(dimethylamino)cycloheptyl]-3,4-dichloroaniline in Part B and proprionic anhydride for propionyl chloride in Part C and heating overnight, there is obtained trans-3,4-dichloro-N-[2-propionoxycycloheptyl]propionanilide; this, on subsequent treatment with one equivalent of potassium hydroxide in ethanol at room temperature, gives trans-3,4-dichloro-N-(2-hydroxycycloheptyl)propionanilide.

C. Preparation of 3,4-dichloro-N-[2-oxocycloheptyl]propionanilide

Treatment of the hydroxyanilide from Part B above with Jones reagent (oxidizing) at room temperature followed by pH neutral work-up procedures gives 3,4-dichloro-N-[2-oxocycloheptyl]propionanilide.

D. Reductive amination of the 2-oxo compound from Part C above

The 3,4-dichloro-N-[2-oxocycloheptyl]propionanilide from Part C above is treated with sodium cyanoborohydride and dimethylamine-dimethylamine hydrochloride in methanol in the presence of 3 Å molecular sieves; the resulting mixture is worked up under basic pH conditions and the organic residue is chromatographed (column) on silica gel to isolate the cis isomer of 3,4-dichloro-N-[2-(dimethylamino)cycloheptyl]propionanilide.

Following the procedure of Example 1 but substituting for the 3,4-dichloroaniline in Part B thereof a stoichiometrically equivalent amount of one of the following substituted anilines:

(a) 3-fluoroaniline,
(b) 4-bromoaniline,
(c) 3-bromoaniline,
(d) 3,5-dichloroaniline,
(e) 3,4-dibromoaniline,
(f) 3-trifluoromethylaniline,
(g) 3,4-dimethylaniline, or
(h) 3-methoxyaniline there are obtained, respectively, (a) N-(2-dimethylaminocycloheptyl)-3-fluoroaniline,
(b) N-(2-dimethylaminocycloheptyl)-4-bromoaniline,
(c) N-(2-dimethylaminocycloheptyl)-3-bromoaniline,
(d) N-(2-dimethylaminocycloheptyl)-3,5-dichloroaniline,
(e) N-(2-dimethylaminocycloheptyl)-3,4-dibromoaniline,
(f) N-(2-dimethylaminocycloheptyl)-3-trifluoromethylaniline,
(g) N-(2-dimethylaminocycloheptyl)-3,4-dimethylaniline, or
(h) N-(2-dimethylaminocycloheptyl)-3-methoxyaniline.

Subsequent reaction of each of these N-(2-dimethylaminocycloheptyl)-substituted anilines with propionyl chloride as in Example 1, Part C, there are obtained respectively:

(a) 3-fluoro-N-(2-dimethylaminocycloheptyl)propionanilide,
(b) 4-bromo-N-(2-dimethylaminocycloheptyl)propionanilide,
(c) 3-bromo-N-(2-dimethylaminocycloheptyl)propionanilide,
(d) 3,5-dichloro-N-(2-dimethylaminocycloheptyl)propionanilide,
(e) 3,4-dibromo-N-(2-dimethylaminocycloheptyl)propionanilide,
(f) 3-trifluoromethyl-N-(2-dimethylaminocycloheptyl)propionanilide,
(g) 3,4-dimethyl-N-(2-dimethylaminocycloheptyl)propionanilide, and
(h) 3-methoxy-N-(2-dimethylaminocycloheptyl)propionanilide.

Following the procedure of Example 1, Part A, but initially substituting stoichiometrically equivalent amounts of pyrrolidine, diethylamine or N-methyl-N',N'-dimethylaminoethylamine hydrochloride for the dimethylamine, there are obtained, respectively:

N-[2-(N-pyrrolidinyl)]cycloheptanediamine,
N-[2-(diethylamino)]cycloheptanediamine, and
N-[2-(N-methyl-N',N'-dimethylaminoethyl)]cycloheptanediamine.

Each of these cycloheptanediamines, when reacted as in Example 1, Part B, with 3,4-dichloroaniline and subsequently as in Example 1, Part C, with propionyl chloride gives:

3,4-dichloro-N-[2-(N-pyrrolidinyl)cycloheptyl]propionanilide,
3,4-dichloro-N-[2-(diethylaminocycloheptyl)]propionanilide, and
3,4-dichloro-N-[2-(N-methyl-N',N'-dimethylaminoethyl)cycloheptyl]propionanilide, respectively.

Following the procedure of Example 1, Part C, but substituting for the propionyl chloride thereof stoichiometrically equivalent quantities:

(a) cyclopropanecarbonyl chloride,
(b) cyclobutanecarbonyl chloride,
(c) cyclopentanecarbonyl chloride,
(d) cyclohexanecarbonyl chloride, or
(e) methoxyacetyl chloride, there are obtained, respectively:

(a) 3,4-dichloro-N-(2-dimethylaminocycloheptyl)cyclopropanecarboxanilide,
(b) 3,4-dichloro-N-(2-dimethylaminocycloheptyl)cyclobutanecarboxanilide,
(c) 3,4-dichloro-N-(2-dimethylaminocycloheptyl)cyclopentanecarboxanilide,
(d) 3,4-dichloro-N-(2-dimethylaminocycloheptyl)cyclohexanecarboxanilide, and
(e) 3,4-dichloro-N-(2-dimethylaminocycloheptyl)methoxyacetanilide.

For oral administration, either solid or fluid unit dosage forms of the selected alkanoylanilide can be prepared. For preparing solid compositions such as tablets, the compound of Formula I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Wafers are prepared in the same manner as tablets, differing only in shape and the inclusion of sucrose or other sweetener and flavor. In their simplest embodiment, capsules, like tablets, are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum, or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions, the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Rectal suppositories as used herein mean solid bodies for insertion into the rectum which melt or soften at body temperature, releasing one or more pharmacologically or therapeutically active ingredients.

Pharmaceutically acceptable substances utilized in rectal suppositories are bases or vehicles and agents to raise the melting point.

Examples of bases or vehicles include, for example, cocoa butter (theobroma oil), glycerin-gelatin, carbowax, (polyoxyethylene glycol) and appropriate mixtures of mono-, di-, and triglycerides of fatty acids. Combinations of the various bases may be used. Agents to raise the melting point of suppositories include, for example, spermaceti and wax. Rectal suppositories may be prepared either by the compressed method or by molding. The usual weight of a rectal suppository is about 2.0 g.

Tablets and capsules for rectal administration are manufactured utilizing the same pharmaceutically acceptable substance and by the same methods as for formulations for oral administration.

Rectal suppositories, tablets or capsules are packaged either individually, in unit-dose, or in quantity, multiple dose, for example, 2, 6, or 12.

The term unit dosage form, as used in the specification and claims, refers to physically discrete units suitable as unitary dosages for mammals including human subjects, each unit containing a predetermined quantity of active material calculated to produce the desired therapeutic effect in association with the required pharmaceutical diluent, carrier, or vehicle. The specifications for the novel unit dosage forms of this invention are dictated by and directly dependent on (a) the unique characteristics of the active material and the particular effect to be achieved, and (b) the limitations inherent in the art of compounding such an active material for use in humans, as disclosed in detail in this specification, these being features of the present invention. Examples of suitable unit dosage forms in accord with this invention are tablets, capsules, pills, suppositories, powder packets, granules, wafers, cachets, teaspoonfuls, tablespoonfuls, dropperfuls, ampuls, vials, segregated multiples of any of the foregoing, and other forms as herein described.

The dosage of the compound for treatment depends on route of administration, the age, weight and condition of the patient. A dosage schedule of from about 4 to about 400 mg., preferably 50 to 200 mg. per day, given in a single dose or in subdivided doses, embraces the effective range to alleviate depression for which the compositions are effective. The dosage to be administered is calculated on the basis of from about 0.08 to about 6 mg./kg. of weight of the subject. The compound is compounded with a suitable pharmaceutical carrier in unit dosage form for convenient and effective administration. In the preferred embodiments of this invention, the dosage units can contain the compound in 5, 10, 25, 30, 50, 100 and 200 mg. amounts for systemic treatment. A sterile preparation of the active material contains 0.1 percent to 25 percent w/v for parenteral treatment. The dosage of compositions containing a compound of formula I and one or more other active ingredients is to be determined with reference to the actual dosage of each such ingredient.

In addition to the administration of a compound of formula I as the principal active ingredient of compositions for treatment of the conditions desired herein, the said compound can be combined with other compounds such as analgesics, for example, aspirin, acetaminophen, PAC compound (phenacetin-aspirin-caffeine), anti-inflammatory agents such as ibuprofen, and the like, anxiolytics such as perphenazine, amitriptylene hydrochloride, chlordiazepoxide, alprazolam, doxepin hydrochloride, and the like.

EXAMPLE 7

A lot of 10,000 tablets, each containing 40 mg. of trans-3,4-dichloro-N-[2-(dimethylamino)cycloheptyl]-propionanilide maleate salt, as the active ingredient compound, is prepared from the following types and amounts of ingredients:

| | |
|---|---|
| Active ingredient compound | 400 g |
| Dicalcium phosphate | 1,500 g |
| Methylcellulose, U.S.P. (15 cps.) | 60 g |
| Talc | 150 g |
| Corn Starch | 200 g |
| Magnesium stearate | 12 g |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in reducing depression in adults at a dose of 1 to 2 tablets per day, depending on the age and weight of the patient.

EXAMPLE 8

One thousand two-piece hard gelatin capsules each containing 50 mg. of 3-bromo-N-[2-(dimethylamino)cycloheptyl]propionanilide, hydrochloride salt as the active ingredient compound are prepared from the following types and amounts of ingredients:

| | |
|---|---|
| Active ingredient compound | 50 g. |
| Lactose | 75 g. |
| Talc | 25 g. |
| Magnesium stearate | 1.5 g. |

The ingredients are mixed well and filled into capsules of the proper size.

Capsules so prepared are useful for treating depression in adults at a dose of one to two capsules per day.

EXAMPLE 9

One thousand tablets for sublingual use are prepared from the following ingredients:

| | |
|---|---|
| 3-trifluoromethyl-N-[2-(dimethylamino)cycloheptyl]propionanilide, micronized | 10 g. |
| Polyethylene glycol 4,000, powdered | 150 g. |
| Polyethylene glycol 6,000, powdered | 75 g. |

The ingredients are mixed well and compressed into sublingual-type tablets.

These tablets (each containing 10 mg. of active ingredient) placed under the tongue are useful to reduce depression with a rapid reduction at a dose of one tablet per six hours.

EXAMPLE 10

Soft gelatin capsules for oral use, each containing 20 mg. of 3,4-dichloro-N-[2-(diethylamino)cycloheptyl]-propionanilide, methanesulfonate salt, are prepared by first dispersing the micronized compound in corn oil to render the material capsulatable and then encapsulating in the usual manner. These capsules are useful in treatment of depression at a dose of one to two capsules a day.

EXAMPLE 11

One thousand tablets, each containing 60 mg. of 3,4-dichloro-N-[2-(N-pyrrolidinyl)cycloheptyl]propionanilide salt, are made from the following types and amounts of ingredients:

| | |
|---|---|
| 3,4-dichloro-[2-(N-pyrrolidinyl)cyclo-heptyl]propionanilide | 60 g. |
| Lactose | 355 g. |
| Microcrystalline cellulose NF | 120 g. |
| Starch | 16 g. |
| Magnesium stearate powder | 4 g. |

The ingredients are screened and blended together and pressed into tablets.

The tablets are useful to overcome depression.

EXAMPLE 12

A sterile preparation suitable for intramuscular injection and containing 80 mg. of 3,4-dichloro-N-[2-(dimethylamino)cycloheptyl]propionanilide, hydrochloride salt, in each milliliter is prepared from the following ingredients:

| | | |
|---|---|---|
| 3,4-dichloro-N-[2-(dimethylamino)-cycloheptyl]propionanilide, hydrochloride | 80 | g. |
| Benzyl benzoate | 200 | ml. |
| Methylparaben | 1.5 | g. |
| Propylparaben | 0.5 | g. |
| Cottonseed oil q.s. | 1,000 | ml. |

One milliliter of this sterile preparation is injected to reduce depression in adults.

EXAMPLES 13 to 25

Following the procedure of the preceding Examples 7 through 12, inclusive, unit dosage forms are similarly prepared substituting equivalent amounts of cis or trans variants of other Formula I compounds; for example

(13) 3-chloro-4-methyl-N-[2-(dimethylamino)cycloheptyl]propionanilide,

(14) 3,4-dichloro-N-{[2-(N-methyl-N-dimethylaminoethyl)amino]cycloheptyl}propionanilide,

(15) 3,4-dimethoxy-N-[2-(dimethylamino)cycloheptyl]propionanilide;

(16) 3-chloro-4-fluoro-N-[2-(dimethylamino)cycloheptyl]propionanilide,

(17) 3,4-dibromo-N-[2-(dimethylamino)cycloheptyl]propionanilide,

(18) 3,4-dimethyl-N-[2-(dimethylamino)cycloheptyl]propionanilide,

(19) 3,4-dichloro-N-[2-(dimethylamino)cycloheptyl]-cyclopropanecarboxanilide,

(20) 3,4-dichloro-N-[2-(dimethylamino)cycloheptyl]-thiopropionanilide,

(21) 3,4-dichloro-N-[2-(N-methyl-N-$\beta$-phenylethylamino)cycloheptyl]propionanilide,

(22) 3,4-dichloro-N-[2-(dimethylamino)cycloheptyl]-propionanilide,

(23) 3-methoxy-N-[2-(dimethylamino)cycloheptyl]-propionanilide,

(24) 3,4-dichloro-N-[2-(diethylamino)cycloheptyl]-propionanilide,

(25) 3,4-dichloro-N-[2-dimethylaminocycloheptyl]-cyclohexanecarboxanilide, or their pharmacologically acceptable acid addition salts for the respective active ingredients in those examples.

The process for treating depression, the pharmaceutical preparation compositions and the compounds per se of this continuation-in-part application, have, within the above generically-described compounds, certain preferred groups of compounds for use according to this invention.

One such preferred group of compounds is that of Formula I above wherein R is $C_1$ to $C_3$-alkyl, $R_1$ is hydrogen or $C_1$ to $C_3$-alkyl, $R_2$ is $C_3$ to $C_6$-(allylic)alkenyl, each of Y and Z is a halogen having an atomic number of from 9 to 35 or one of Y and Z is a $C_1$ to $C_2$-alkyloxy in the 3-position and the other of Y and Z is hydrogen, a $C_1$ to $C_2$-alkyloxy in the 4-position, or a halogen having an atomic number of from 9 to 35, or a pharmaceutically acceptable salt thereof. Examples of such preferred compounds are:

3,4-dichloro-N-[2-(N-allyl-N-methylamino)cycloheptyl]propionanilide;

3,4-dichloro-N-[2-(N-allylamino)cycloheptyl]propionanilide;

3-methoxy-N-[2-(N-allyl-N-methylamino)cycloheptyl]propionanilide;

3,4-dimethoxy-N-[2-(N-allyl-N-methylamino)cycloheptyl]propionanilide;

3-chloro-4-methoxy-N-[2-(N-allyl-N-methylamino)-cycloheptyl]acetanilide;

4-chloro-3-methoxy-N-[2-(N-allylamino)cycloheptyl]propionanilide;

and the pharmacologically acceptable salts thereof.

Another preferred sub-group of these compounds is that of Formula I above wherein R is $C_1$ to $C_3$-alkyl, $R_1$ is hydrogen or $C_1$ to $C_3$-alkyl, $R_2$ is —$CH_2C_6H_5$(benzyl) or —$CH_2CH_2C_6H_5$(phenethyl), each of Y and Z is a halogen having an atomic number of from 9 to 35, or one of Y and Z is a $C_1$ to $C_2$-alkyloxy in the 3-position and the other of Y and Z is hydrogen, a $C_1$ to $C_2$-alkyloxy in the 4-position or a halogen having an atomic number of from 9 to 35, and the pharmacologically acceptable salts thereof. Examples of such compounds include:

3,4-dichloro-N-[2-(N-$\beta$-phenethyl-N-methylamino)-cycloheptyl]propionanilide;

3,4-dichloro-N-[2-(N-benzyl-N-methylamino)cycloheptyl]propionanilide;

3,4-dibromo-N-[2-(N-benzyl-N-ethylamino)cycloheptyl]acetanilide;

3-methoxy-N-[2-(N-$\beta$-phenethyl-N-methylamino)cycloheptyl]propionanilide;

3,4-dimethoxy-N-[2-(N-benzyl-N-methylamino)cycloheptyl]propionanilide;

4-chloro-3-methoxy-N-[2-(N-β-phenethylamino)cycloheptyl]propionanilide;

3,4-difluoro-N-[2-(N-benzylamino)cycloheptyl]propionanilide;

and the pharmacologically acceptable salts thereof.

These compounds can be substituted into the above-described pharmaceutical formulation examples as the essential active antidepressant ingredient in chemically-equivalent amounts. For example, the compounds 3,4-dichloro-N-[2-(N-allylamino)cycloheptyl]propionanilide, or 3,4-dichloro-N-[2-(N-benzylamino)cycloheptyl]propionanilide, or a pharmacologically acceptable acid addition salt thereof, can be used.

Some of the compounds of Formula I in claim 1 are new and are claimed herein per se. For example, those compounds wherein p, Q, Y and Z are as defined herein, and wherein R is as defined in claim 1, $R_1$ is hydrogen or $C_1$ to $C_3$-alkyl and $R_2$ is $C_3$ to $C_6$-allylic alkenyl are new and are not suggested by the prior art.

Also, those compounds of Formula I in claim 1, wherein p, Q, Y and Z are as defined in claim 1, R is vinyl, $C_3$ to $C_6$-cycloalkyl, ethoxy or methoxymethyl, $R_1$ is hydrogen or $C_1$ to $C_3$-alkyl, and $R_2$ is $C_3$ to $C_6$-allylic alkenyl, benzyl or 2-phenyl ethyl are also new and are claimed herein per se.

The trans compounds wherein one of $R_1$ and $R_2$ is hydrogen, the other of $R_1$ and $R_2$ is $C_3$ to $C_6$-(allylic)alkenyl, benzyl or phenethyl, as defined above, and p, Q, R, Y and Z are as defined above, are prepared in the manner described below:

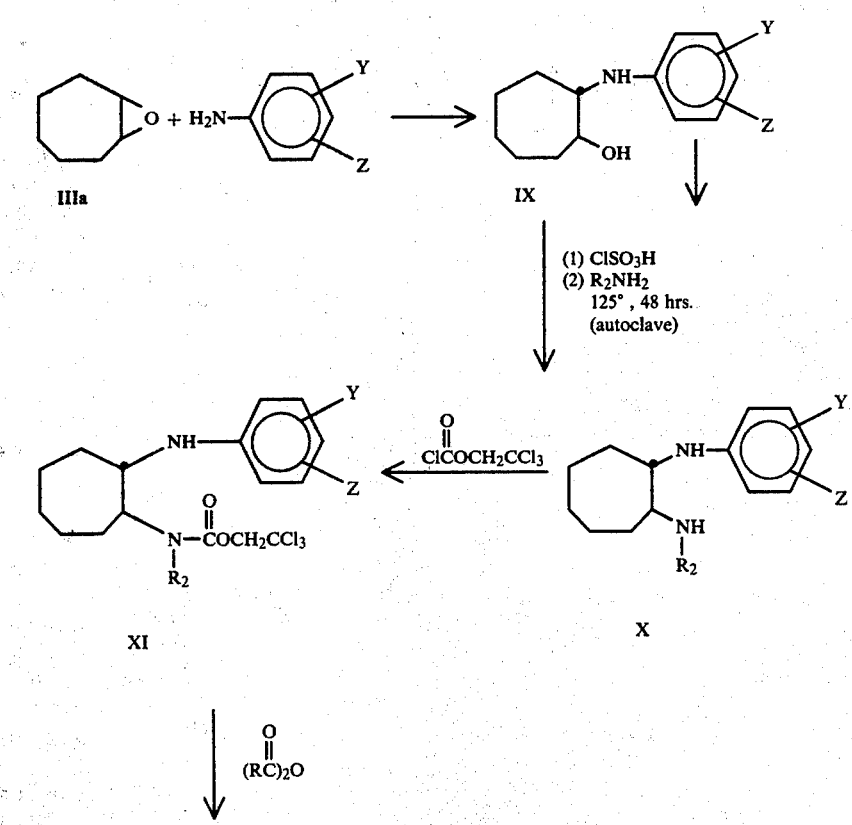

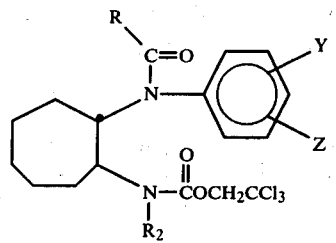

XII

↓ Zn acetic acid

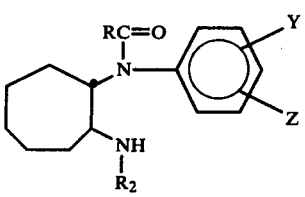

XIII

Reaction of the cycloheptane oxide IIIa with an aniline under conditions well known in the art gives the N-(2hydroxycyclopentyl)aniline IX which, when reacted with chlorosulfonic acid in a non-polar organic solvent, e.g., methylene chloride, at 20°–30° C. followed by heating with a selected $R_2$-amine (aqueous) at 100°–150° C. for 40–55 hours at elevated pressure (2–10 atm.), gives the diamine X. Reaction of diamine X with 2,2,2-trichloroethyl chloroformate, or equivalent N-blocking compound, at 20°–30° C. for 1–5 hours proceeds in the presence of an acid scavenger, e.g., triethylamine, to give the 2-(N-blocked amino) compound XI. Acylation of the N-blocked compound XI with the selected acid anhydride,

by heating at 90°–120° C. for 12 to 30 hours gives the N-blocked anilide XII. Deprotection of the 2-amino function of the 2-N-blocked anilide XII is then accomplished by reaction with an N-deblocking agent such as metal dust in acid, e.g., zinc in acetic acid, in a polar organic solvent, e.g., methanol, at 20°–100° C. for 2 to 6 hours. Work-up, isolation and purification procedures are those standard in the art of organic chemistry.

Preparation of the cis isomeric compound XIV is carried out as described previously

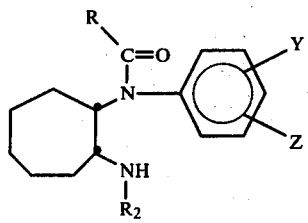

XIV

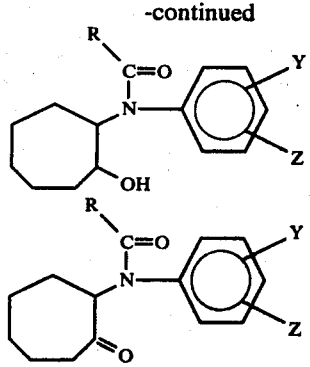

in this specification by oxidation of the 2-hydroxycyclopentylanilide XV with a known oxidizing agent, e.g., Jones Reagent, to the ketone XVI, which, when reacted with a $C_3$ to $C_6$-(allylic)alkenyl, benzyl or β-phenethyl amine in the presence of a reducing agent, e.g., sodium cyanoborohydride, gives mixed isomer amino anilide XVII.

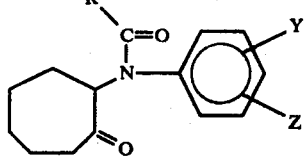

XVII

Chromatographic separation of the two isomers can be effected to give the cis amino anilide XIV, wherein $R_2$ is the $C_2$ to $C_6$-(allylic)alkenyl, benzyl or phenethyl group.

These compounds, having a mono-$C_3$ to $C_6$-(allylic)alkenyl, benzyl or β-phenethyl substituted amino group in the 2-position of the cyclopentyl ring, have anti-depressant properties in standard laboratory animal tests such as the standard yohimbine toxicity potentiation and oxotremorine hypothermia antagonism tests, indicating quite potent anti-depressant properties of these compounds so that 2-(N-allylamino-, 2-(N-benzylamino- and 2-(N-phenethylamino)cycloheptyl anilides have similar properties and uses as the above-described N-[2-(N,N-disubstituted-amino)cycloheptyl]anilide compounds in about the same dosage ranges as indicated above.

EXAMPLE 26

Trans-3,4-dichloro-N-[2-(N-allylamino)cycloheptyl]-propionanilide

A. Preparation of trans-3,4-dichloro-N-[2-(N-allylamino)cycloheptyl]aniline

A mixture of 0.20 mole of 3,4-dichloro-N-(2-sulfocyclohepyl)aniline and 250 ml. of a 50 percent allylamine in water solution is heated at 125° C. in an autoclave for forty-eight hours. The resulting reaction mixture is washed from the autoclave 1500 ml. solution of methanol. This solution is evaporated until material therefrom oils out as a separate layer. The oil is extracted with 500 ml. of methylene chloride. The organic layer is washed with saturated sodium chloride solution, dried over magnesium sulfate and evaporated to an orange oil. The oil is chromatographed on 600 ml. of silica gel eluting with 2 liters of chloroform and 4 liters of ethyl acetate. The ethyl acetate fraction is separated and evaporated to an oil; the trans-3,4-dichloro-N-[2-(N-allylamino)cycloheptyl]aniline. This amine oil is converted to its hydrochloride salt with excess ether-hydrogen chloride mixture and recrystallized from a mixture of 450 ml. of methanol and about 2000 ml. of ethyl ether to obtain trans-3,4-dichloro-N-[2-(N-allylamino)cycloheptyl]aniline hydrochloride.

B. Preparation of trans-3,4-dichloro-N-[2-(N-allyl-N-trichloroethoxycarbonylamino)cycloheptyl]aniline and its hydrochloride To a mixture of 0.05 mole of the above trans-3,4-dichloro-N-[2-(N-allylamino)cycloheptyl]aniline, released from its hydrochloride salt and 5.5 g. (0.05 mole) of triethylamine in 400 ml. of ethyl ether, there is added dropwise 10.6 g. (0.05 mole) of 2,2,2-trichloroethyl chloroformate in 50 ml. of ethyl ether while cooling the reaction vessel in ice in thirty minutes. The mixture is then stirred overnight at room temperature. The next day 250 ml. of saturated sodium bicarbonate solution is added. The organic layer is then separated and washed with saturated sodium chloride solution, dried over magnesium sulfate and evaporated to an oil. This is the crude sub-titled amine. A 1.0 g. portion of this amine oil is converted to its hydrochloride salt with excess ethereal hydrogen chloride and the salt is recrystallized from a mixture of 15 ml. of methanol and 80 ml. of ethyl ether to obtain the trans-3,4-dichloro-N-[2-(N-allyl-N-trichloroethoxycarbonylamino)cycloheptyl]anilide hydrochloride.

C. Preparation of trans-3,4-dichloro-N-[2-(N-allyl-N-trichloroethoxycarbonylamino)cycloheptyl]propionanilide A mixture of 0.05 mole of trans-3,4-dichloro-N-[2-(N-allyl-N-trichloroethoxycarbonylamino)cycloheptyl]aniline and 50 ml. of propionic acid anhydride is heated on a steam bath overnight. Then 250 ml. of water is added and the heating is continued for 0.5 hours. The mixture is cooled, made basic with 15 percent sodium hydroxide solution and then extracted with ethyl ether. The organic layer is washed with saturated sodium chloride solution, dried over magnesium sulfate and evaporated to a brown oil weighing. 24.5 g., the sub-titled propionanilide, which is used without purification in the next step.

D. Preparation of trans-3,4-dichloro-N-[2-(N-allylamino)cycloheptyl]propionanilide A mixture of the above prepared trans-3,4-dichloro-N-[2-N-allyl-N-trichloroethoxycarbonylamino)cycloheptyl]propionanilide (about 0.05 mole) and 32.7 g. (0.50 mole) of zinc dust in 250 ml. of 5 percent acetic acid in methanol (v/v) is stirred overnight at room temperature. The resulting reaction mixture is then filtered through a filter aid (Celite ®) and evaporated to an oil. The oil residue is treated with 100 ml. of 15 percent sodium hydroxide solution and 300 ml. of methylene chloride. The mixture is then filtered to remove the excess zinc and zinc hydroxide. The organic layer is then washed with saturated sodium chloride, dried over magnesium sulfate and evaporated to a yellow oil, the named product which is then converted to its oxalic acid salt and analyzed as the salt.

I claim:

1. A process for treating depression which comprises administering to a depressed human a compound of the formula wherein the wavy line (~) in the 1-position of the cycloheptyl ring indicates cis or trans configuration of the substituents in the 1- and 2-positions of the cyclopentyl ring;

p is zero or 1;

Q is oxygen or sulfur;

R is $C_1$ to $C_3$-alkyl, vinyl, $C_3$ to $C_6$-cycloalkyl, ethoxy, or methoxymethyl;

$R_1$ is hydrogen or $C_1$ to $C_3$-alkyl;

$R_2$ is:
 —$CH_2C_6H_5$,
 —$CH_2CH_2$—$C_6H_5$, or
 $C_3$-$C_6$(allylic)alkenyl;

each of Y and Z is selected from the group consisting of hydrogen, a halogen having an atomic number of from 9 to 35, trifluoromethyl, $C_1$ to to $C_2$-alkyl, and $C_1$ to $C_2$-alkyloxy and when Y is trifluoromethyl, Z is hydrogen; when Y is $C_1$ to $C_2$-alkyloxy and Z is hydrogen, the $C_1$ to $C_2$-alkyloxy is in the 3-position; when Y and Z are both halogens or $C_1$ to $C_2$-alkyloxy, they are present in the 3-and 4- or 3- and 5-positions, or a pharmacologically acceptable salt thereof, in an amount ranging from about 4 to about 400 mg. per dosage unit to alleviate the conditions of depression, in association with a pharmaceutical carrier.

2. A process in accordance with claim 1 wherein the compound of formula I is administered in unit dosage form ranging from 1 to 100 mg of the formula I compound or its pharmacologically acceptable acid addition salt.

3. A process according to claim 1 wherein the compound of formula I therein is one wherein R is $C_1$ to $C_3$-alkyl, $R_1$ is hydrogen or $C_1$ to $C_3$-alkyl, $R_2$ is $C_3$ to $C_6$-allylic alkenyl, each of Y and Z is a halogen having an atomic number of from 9 to 35, or one of Y and Z is $C_1$ to $C_2$-alkyloxy in the 3-position and the other of Y and Z is hydrogen, $C_1$ to $C_2$-alkyloxy in the 4-position, or a halogen having an atomic number of from 9 to 35, or a pharmacologically acceptable salt thereof.

4. A process according to claim 3 wherein the compound of formula I therein is 3,4-dichloro-N-[2-(N-allyl-N-methylamino)cycloheptyl]propionanilide, or a pharmacologically acceptable salt thereof.

5. A process according to claim 3 wherein the compound of formula I therein is 3,4-dichloro-N-[2-(N-allylamino)cycloheptyl]propionanilide or a pharmacologically acceptable salt thereof.

6. A process according to claim 1 wherein the compound of formula I therein is one wherein R is $C_1$ to $C_3$-alkyl, $R_1$ is hydrogen or $C_1$ to $C_3$-alkyl, $R_2$ is —$CH_2C_6H_5$ or —$CH_2CH_2C_6H_5$, each of Y and Z is a halogen having an atomic number of from 9 to 35, or one of Y and Z is $C_1$ to $C_2$-alkyloxy in the 3-position and the other of Y and Z is hydrogen, $C_1$ to $C_2$-alkyloxy in the 4-position, or a halogen having an atomic number of from 9 to 35, or a pharmacologically acceptable salt thereof.

7. A process according to claim 6 wherein the compound of formula I in claim 6 therein is 3,4-dichloro-N-[2-(N-β-phenethyl-N-methylamino)cycloheptyl]propionanilide, or a pharmacologically acceptable salt thereof.

8. A process according to claim 6 wherein the compound of formula I therein is 3,4-dichloro-N-[2-(N-benzyl-N-methylamino)cycloheptyl]propionanilide, or a pharmaceutically acceptable salt thereof.

9. A pharmaceutical preparation in dosage unit form adapted for administration to obtain an anti-depression effect comprising per dosage unit an anti-depressant effective, non-toxic amount of a compound of the formula

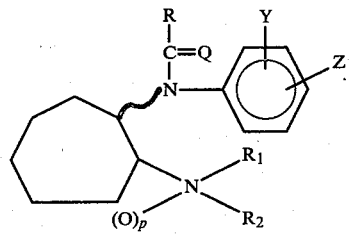

wherein the wavy line (~) in the 1-position of the cyclopentyl ring indicates cis or trans configuration of the substituents in the 1- and 2-positions of the cyclopentyl ring;
P is zero or 1;
Q is oxygen or sulfur;
R is $C_1$ to $C_3$-alkyl, vinyl, $C_3$ to $C_6$-cycloalkyl, ethoxy, or methoxymethyl;
$R_1$ is hydrogen or $C_1$ to $C_3$-alkyl;
$R_2$ is:

—$CH_2C_6H_5$,
—$CH_2CH_2C_6H_5$, or
$C_3$ to $C_6$-(allylic)alkenyl;
each of Y and Z is selected from the group consisting of hydrogen, a halogen having an atomic number of from 9 to 35, trifluoromethyl, $C_1$ to to $C_2$-alkyl, and $C_1$ to $C_2$-alkyloxy and when Y is trifluoromethyl, Z is hydrogen; when Y is $C_1$ to $C_2$-alkyloxy and Z is hydrogen, the $C_1$ to $C_2$-alkyloxy is in the 3-position; when Y and Z are both halogens or $C_1$ to $C_2$-alkyloxy, they are present in the 3-and 4- or 3- and 5-positions, or a pharmacologically acceptable salt thereof, in an amount ranging from about 4 to about 400 mg. per dosage unit to alleviate the conditions of depression, in association with a pharmaceutical carrier.

10. A pharmaceutical preparation according to claim 9 wherein the compound of formula I is in the trans configuration.

11. A pharmaceutical preparation according to claim 9 wherein the compounds of formula I is in the cis configuration.

12. A pharmaceutical preparation according to claim 9 wherein the compound of formula I therein is one wherein R is $C_1$ to $C_3$-alkyl. $R_1$ is hydrogen or $C_1$ to $C_3$-alkyl, $R_2$ is $C_3$ to $C_6$-allylic alkenyl, each of Y and Z is a halogen having an atomic number of from 9 to 35, or one of Y and Z is $C_1$ to $C_2$-alkyloxy in the 3-position and the other of Y and Z is hydrogen, $C_1$ to $C_2$-alkyloxy in the 4-position, or a halogen having an atomic number of from 9 to 35, or a pharmacologically acceptable salt thereof.

13. A pharmaceutical preparation according to claim 12 wherein the compound of formula I therein is 3,4-dichloro-N-[2-(N-allyl-N-methylamino)cycloheptyl]propionanilide, or a pharmacologically acceptable salt thereof.

14. A pharmaceutical preparation according to claim 13 wherein the compound of formula I therein is 3,4-dichloro-N-[2-(N-allylamino)cycloheptyl]propionanilide, or a pharmacologically acceptable salt thereof.

15. A pharmaceutical preparation according to claim 9 wherein the compound of formula I therein is one wherein R is $C_1$ to $C_3$-alkyl, $R_1$ is hydrogen or $C_1$ to $C_3$-alkyl, $R_2$ is —$CH_2C_6H_5$ or —$CH_2CH_2C_6H_5$, each of Y and Z is a halogen having an atomic number of from 9 to 35, or one of Y and Z is $C_1$ to $C_2$-alkyloxy in the 3-position and the other of Y and Z is hydrogen, $C_1$ to $C_2$-alkyloxy in the 4-position, or a halogen having an atomic number of from 9 to 35, or a pharmacologically acceptable salt thereof.

16. A pharmaceutical preparation according to claim 15 wherein the compound of formula I in claim 15 therein is 3,4-dichloro-N-[2-(N-β-phenethyl-N-methylamino)cycloheptyl]propionanilide, or a pharmacologically acceptable salt thereof.

17. A pharmaceutical preparation according to claim 15 wherein the compound of formula I therein is 3,4-dichloro-N-[2-(N-benzyl-N-methylamino)cycloheptyl]propionanilide, or a pharmacologically acceptable salt thereof.

18. A compound of the formula

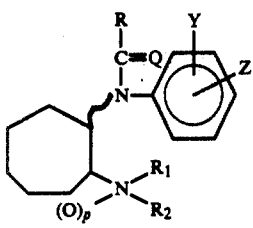

(I)

wherein the wavy line (∼) in the 1-position of the cyclopentyl ring indicates cis or trans configuration of the substituents in the 1- and 2-positions of the cyclopentyl ring;

p is zero or 1;
Q is oxygen or sulfur;
R is $C_1$ to $C_3$-alkyl, vinyl $C_3$ to $C_6$-cycloalkyl, ethoxy, or methoxymethyl;
$R_1$ is hydrogen or $C_1$ to $C_3$-alkyl;
$R_2$ is $C_3$ to $C_6$-(allylic)alkenyl;
each of Y and Z is selected from the group consisting of hydrogen, a halogen having an atomic number of from 9 to 35, trifluoromethyl, $C_1$ to $C_2$-alkyl, and $C_1$ to $C_2$-alkyloxy and when Y is trifluoromethyl, Z is hydrogen; when Y is $C_1$ to $C_2$-alkyloxy and Z is hydrogen, the $C_1$ to $C_2$-alkyloxy is in the 3-position; when Y and Z are both halogens or $C_1$ to $C_2$-alkyloxy, they are present in the 3- and 4- or 3- and 5-positions, or an acid addition salt thereof.

19. A compound according to claim 18 wherein the compound of formula I is in the trans configuration.

20. A compound according to claim 18 wherein the compound of formula I is in the cis configuration.

21. 3,4-Dichloro-N-[2-(N-allyl-N-methylamino)-cyloheptyl]propionanilide and the acid addition salts thereof.

22. 3,4-Dichloro-N-[2-(N-β-phenethyl-N-methylamino)cycloheptyl]propionanilide and the acid addition salts thereof.

23. 3,4-Dichloro-N-[2-(N-benzyl-N-methylamino)cycloheptyl]propionanilide, and the acid addition salts thereof.

24. A compound of the formula

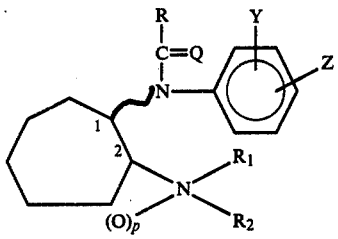

(1)

wherein the wavy line (∼) in the 1-position of the cycloheptyl ring indicates cis or trans configuration of the substituents in the 1- and 2-positions of the cyclopentyl ring;

P is zero or 1;
Q is oxygen or sulfur;
R is vinyl, $C_3$ to $C_6$-cycloalkyl, ethoxy, or methoxymethyl;
$R_1$ is hydrogen or $C_1$ to $C_3$-alkyl;
$R_2$ is $C_3$ to $C_6$-(allylic)alkenyl), benzyl or phenylethyl,
each of Y and Z is selected from the group consisting of hydrogen, a halogen having an atomic number of from 9 to 35, trifluoromethyl, $C_1$ to $C_2$-alkyl, and $C_1$ to $C_2$-alkyloxy and when Y is trifluoromethyl, Z is hydrogen, when Y is $C_1$ to $C_2$-alkyloxy and Z is hydrogen, the $C_1$ to $C_2$-alkyloxy is in the 3-position, when Y and Z are both halogens or $C_1$ to $C_2$-alkyloxy, they are present in the 3- and 4- or 3- and 5-positions, or a pharmacologically acceptable salt thereof.

* * * * *